United States Patent [19]
Weckström

[11] Patent Number: 5,913,249
[45] Date of Patent: Jun. 15, 1999

[54] MEASURING DETECTOR AND SYSTEM FOR THE MEASUREMENT OF GAS FLOW

[75] Inventor: Kurt Weckström, Helsinki, Finland

[73] Assignee: Instrumentarium Oy, Helsinki, Finland

[21] Appl. No.: 08/885,550

[22] Filed: Jun. 30, 1997

[30] Foreign Application Priority Data

Jul. 2, 1996 [FI] Finland ..................................... 962729

[51] Int. Cl.[6] ................................................ G01F 1/32
[52] U.S. Cl. .............................................. 73/861.52
[58] Field of Search ........................... 73/861.52, 861.65; 600/538, 539; 128/725

[56] References Cited

U.S. PATENT DOCUMENTS

| | | |
|---|---|---|
| 4,403,514 | 9/1983 | Osborn . |
| 5,088,332 | 2/1992 | Merilainen et al. ................. 73/861.65 |
| 5,111,827 | 5/1992 | Rantala .................... 128/719 |
| 5,277,196 | 1/1994 | Hankinson et al. .................... 128/725 |
| 5,379,650 | 1/1995 | Kofoed et al. . |

FOREIGN PATENT DOCUMENTS

| | | |
|---|---|---|
| 228762 | 7/1987 | European Pat. Off. . |
| 552916 | 7/1993 | European Pat. Off. . |
| 2306346 | 5/1997 | United Kingdom . |

*Primary Examiner*—George Dombroske
*Assistant Examiner*—Jewel V. Thompson
*Attorney, Agent, or Firm*—Andurs, Sceales, Starke & Sawall

[57] ABSTRACT

Measuring detector and system for the measurement of gas flow, especially for the measurement of the pressure and/or flow of a patient's respiratory gas. The surface of the wall (2) of a flow channel (1) and/or the surface of a restricting element (3), said surface being in direct contact with the gas flow to be measured, is provided with an agent for reducing the contact angle ($\theta$) of a water drop or a drop containing water to said surface in relation to the contact angle formed between a corresponding water drop and a corresponding surface not treated with such agent.

45 Claims, 3 Drawing Sheets

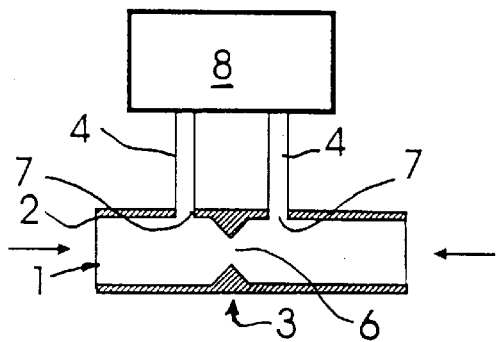
Fig. 1
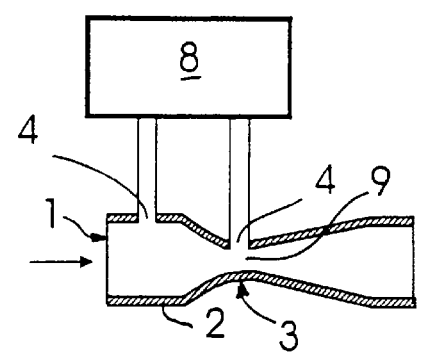
Fig. 2
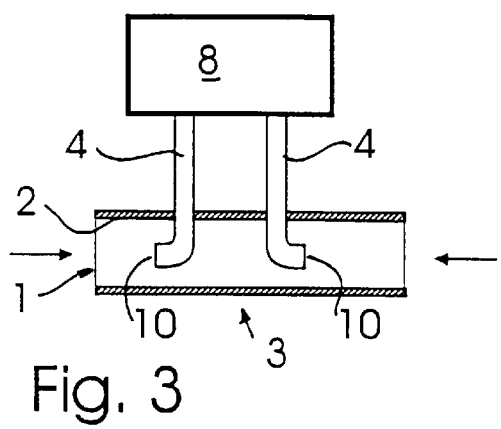
Fig. 3
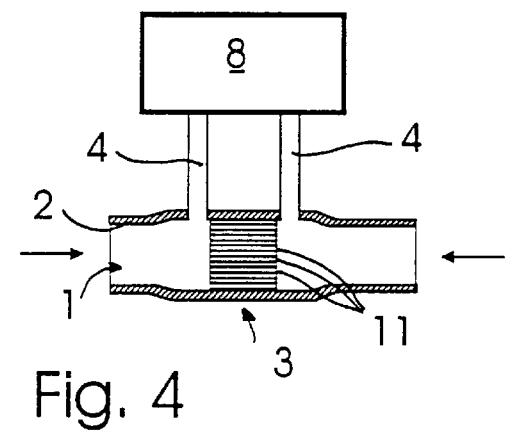
Fig. 4
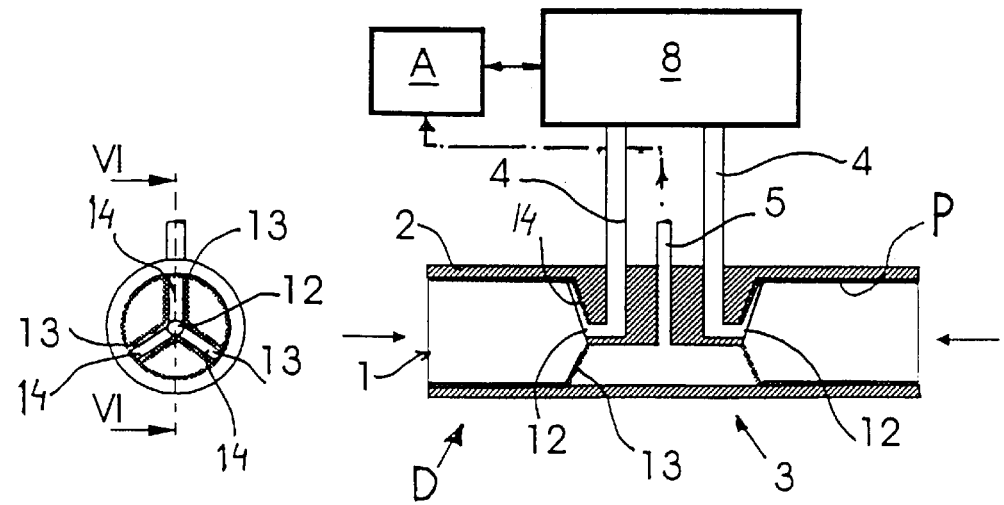
Fig. 5
Fig. 6

MEASURING DETECTOR AND SYSTEM FOR THE MEASUREMENT OF GAS FLOW

BACKGROUND OF THE INVENTION

The present invention relates to a measuring detector for the measurement of gas flow, especially for the measurement of the pressure and/or flow of a patient's respiration. Moreover, the invention relates to a system for the measurement of the pressure and/or flow of a patient's respiration.

In hospitals, during intensive care and operations, respiration apparatus must be used to take care of the patients' respiration. Unhindered flow of gases into and from the patient's lungs is naturally of vital importance. The condition of the gas channels can be monitored both by measuring the concentrations of the exhalation gases and by measuring the flow and pressure of the gases. Especially, monitoring of the carbon dioxide content of exhalation gas is widely used as a routine in operating theatres. However, measurement of flow and pressure are essential additional functions both in respect of safety and because they make it possible to calculate quantities descriptive of the mechanical operation and respiratory metabolism of the lungs.

In principle, there are many applicable types of flow detectors. However, measurements in clinical conditions involve many problems. The flow is measured from the end of a so-called intubation tube inserted into the patient's windpipe. The detector is therefore exposed to both humidity and mucous secretions coming from the windpipe. It is clear that such soiling is likely to affect the operation of especially the commonly used turbine and hot-wire detectors. Ultrasonic detectors are better able to tolerate soiling, but they are dependent on changes of the flow profile, temperature and gas composition, requiring sophisticated compensation. Differential pressure detectors are better suited for clinical use. The flow in the tube may be laminar or turbulent. In the case of laminar flow, the pressure difference across a flow restricting element placed in the tube is directly proportional to the flow. In the case of a turbulent flow, the pressure difference depends on the square of the flow. In addition, the pressure difference depends on the square of the cross-sectional area of the flow tube. The detectors currently used are generally made of plastic, and the concentration of water forms small drops on the interior walls of the flow detector because water has a large contact angle to a plastic surface. The problem is that the condensed water together with possible secretions gathered in it reduce the cross-sectional area of the detector, resulting in an increase in the measured pressure difference. If the measured pressure difference is too large, this also means that the calculated flow value is too high and therefore incorrect. A detector with a small cross-sectional area is the most sensitive in this respect. In short-time use of the measuring detector the resulting error is generally not too large, but if the detector is used continuously e.g. for one or more hours in humid conditions, the error produced in the measurement results will be considerable. One way to eliminate this problem is to heat the detector to a temperature sufficient to prevent condensation. However, this method requires a heating element and an electric connection, so it is difficult to use in practice and a detector with a heating element is also expensive to fabricate. Moreover, a hot element may involve a danger to the patient.

BRIEF SUMMARY OF THE INVENTION

The object of the present invention is to eliminate the problems described above.

A specific object of the invention is to present an improved detector restricting the flow of respiratory gas which is not sensitive to condensed water and the patient's mucous secretions and which is capable of reliable operation even in dirty conditions. A further object of the invention is to present a system correspondingly improved for the measurement of the pressure and/or flow of a patient's respiration.

The measuring detector of the invention comprises a tubular flow channel for guiding the gas flow to be measured, which flow channel is delimited by a wall; a restricting element disposed in the flow channel to restrict gas flow in the flow channel; and measuring channels opening into the flow channel for the measurement of the pressure difference caused by the restricting element.

According to the invention, the surface of the flow channel wall and/or the restricting element, said surface being in direct contact with the gas flow to be measured, is provided with an agent for reducing the contact angle of a water drop or a drop containing water to said surface in relation to the contact angle formed between a corresponding surface not treated with such agent and a corresponding water drop.

The system of the invention comprises an intubation tube designed to be inserted into a patient's windpipe; a measuring detector connected to the intubation tube and comprising a tubular flow channel for guiding the gas flow to be measured, said flow channel being delimited by a wall; a restricting element disposed in the flow channel to restrict gas flow in the flow channel; a measuring device for measuring the pressure difference caused by the restricting element; and measuring channels opening into the flow channel for passing the pressure from the flow channel into the measuring device.

According to the invention, the surface of the flow channel wall and/or the restricting element, said surface being in direct contact with the gas flow to be measured, is provided with an agent for reducing the contact angle of a water drop or a drop containing water to said surface in relation to the contact angle formed between a corresponding surface not treated with such agent and a corresponding water drop.

The invention is based on the principle of reducing the contact angle between water and the detector material sufficiently to cause the condensed water drops to spread along the interior surface of the measuring detector, thus preventing excessive reduction of the cross-sectional area of the detector. Therefore, even small water drops quickly combine with each other, forming a continuous film which can flow out of the detector. The flow reading will remain within the set tolerance limit for a long time, which is important especially in intensive care. The contact angle of a water drop can be determined by the so-called sessile-drop method.

In an embodiment of the measuring detector and system, the agent reduces the surface energy of a drop.

In an embodiment of the measuring detector and system, the agent increases the surface energy of the surface in question.

In an embodiment of the measuring detector and system, the agent is a surface-active agent that reduces the surface energy of a drop.

In an embodiment of the measuring detector and system, the agent is an antifogging agent which is immobilized on the surface in question. In an embodiment of the measuring detector, the surface-active agent is an antifogging agent. The antifogging agent used may be e.g. Dr. Fog (fabricated by O.R.Concepts, Inc., U.S.A.), which is a commercially available antifogging agent designed for antifogging treatment of lenses used in endoscopic apparatus. Also, the antifogging agents mentioned in specification U.S. Pat. No. 3,068,100, used for antifogging treatment of film material, may be usable.

In an embodiment of the measuring detector and system, the agent is applied as a film-like coating onto the surface in question.

In an embodiment of the measuring detector and system, the coating formed from the agent is immobilized on the surface.

In an embodiment of the measuring detector and system, the material of the wall and/or restricting element is impregnated with the agent.

In an embodiment of the measuring detector and system, the agent is so selected that the contact angle of a water drop or a drop containing water to the surface in question will be smaller than 30°, appropriately smaller than 20°, preferably smaller than 10°, most advantageously about 0°.

In an embodiment of the measuring detector and system, the agent is a surface-active agent soluble in water.

In an embodiment of the measuring detector and system, the surface-active agent comprises molecules containing an oleo-philic hydrophobic group, such as an alkyl chain, and a hydrophilic group, such as a negatively charged carboxylic or sulphonic acid group. The surface-active agent may be e.g. a dioctyl sodium sulfosuccinate, which are available under several commercial trademarks and which are used as moistening agents e.g. in medical and cosmetic industry and in foodstuffs.

In an embodiment of the measuring detector and system, the surface-active agent contains a detergent, such as soap or the like.

In an embodiment of the measuring detector and system, the measuring detector is a spirometer connected to an intubation tube inserted into the patient's windpipe. Incorporated in the same piece there may also be a measuring channel functioning as a sampler for a gas analyzer. The measuring channel can also be coated with a surface-active agent.

An embodiment of the measuring detector and system comprises a measuring channel connected to the measuring detector and functioning as a sampler for a gas analyzer.

In an embodiment of the measuring detector and system, the measuring detector works on the Pitot tube principle, based on the measurement of Pitot pressure, in which the flow restricting element comprises one or more vanes directed against the flow.

In an embodiment of the measuring detector and system, the restricting element is provided with vanes arranged radially around the orifice of the measuring channel, and each vane is provided with a groove for directing the gas flow hitting the vanes into the orifice.

In an embodiment of the system, the system comprises a gas analyzer for the determination of the composition of respiratory gas.

In an embodiment of the system, the measuring channel functioning as a sampler for a gas analyzer is disposed between the intubation tube and a respiration apparatus.

In an embodiment of the system, the measuring channel functioning as a sampler for a gas analyzer is disposed between a respiration apparatus and the patient.

BRIEF DESCRIPTION OF THE SEVERAL VIEWS OF THE DRAWINGS

In the following, the invention is described in detail by the aid of a few examples of its embodiments by referring to the attached drawing, in which FIG. 1 is a diagram representing a first embodiment of the measuring detector of the invention in longitudinal section, FIG. 2 is a diagram representing a second embodiment of the measuring detector of the invention in longitudinal section, FIG. 3 is a diagram representing a third embodiment of the measuring detector of the invention in longitudinal section, FIG. 4 is a diagram representing a fourth embodiment of the measuring detector of the invention in longitudinal section, FIG. 5 is a diagram representing a fifth embodiment of the measuring detector of the invention in longitudinal section, FIG. 6 presents section VI—VI of FIG. 5.

DETAILED DESCRIPTION OF THE INVENTION

Figure 7:
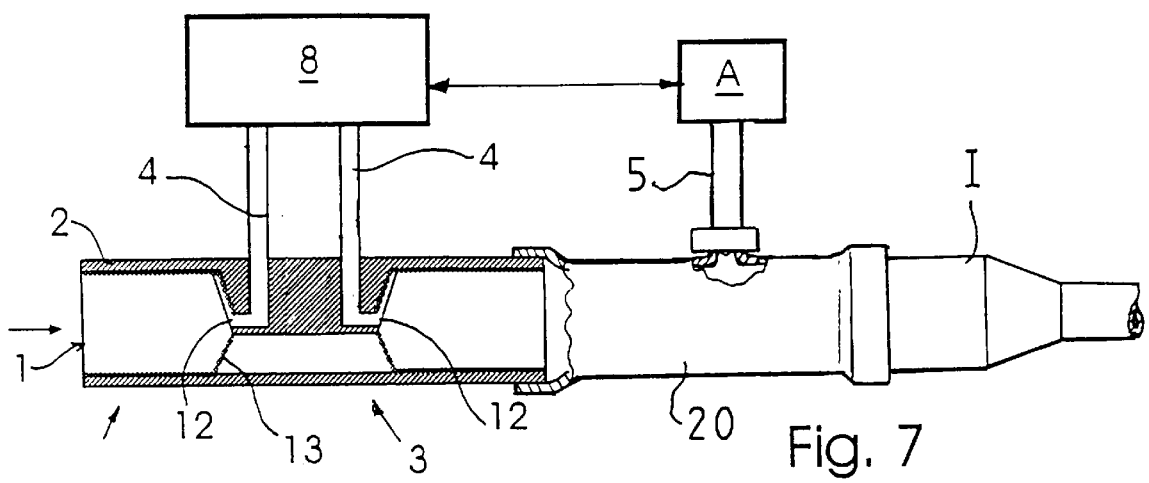
FIG. 7 is a diagram representing a sixth embodiment of the measuring detector of the invention in longitudinal section.

FIG. 1–7 present different types of measuring detectors with flow restriction, designed for the measurement of gas flow, which can be improved with a coating of an agent according to the invention. The main types of flow detector and their principles are presented e.g. in the publication Doebelin: Measurement Systems, McGraw-Hill Kogakusha, 1976, which is referenced here.

The measuring detectors presented in FIG. 1–7 comprise a tubular flow channel 1 for passing a gas flow to be measured. The flow channel is delimited by a wall 2. The flow channel is provided with a restricting element 3 to restrict gas flow in the flow channel 1. Communicating with the flow channel 1 are measuring channels 4, which are connected to a measuring device for the measurement of the pressure difference created in the flow channel by the action of the flow restricting element 3. The surface of the flow channel 1 wall 2 and/or restricting element 3, said surface being in direct contact with the gas flow to be measured, is provided with an agent for reducing the contact angle $\theta$ of a water drop or a drop containing water to said surface in relation to the contact angle formed between a corresponding surface not treated with such agent and a corresponding drop. As to its action, the agent may either reduce the surface energy (surface tension) of the drop, or alternatively the agent may increase the surface energy of said surface.

In the embodiment illustrated by FIG. 1, the restricting element 3 restricting the flow in the flow channel 1 is an aperture 6, with the orifices 7 of the pressure measuring channels 4 on both sides of it. These orifices are connected via measuring channel tubes 4 to a measuring device 8, which is an element measuring pressure difference. As to its shape, the aperture 6 may have different appearances as stated in the above-mentioned publication, but its sensitivity to condensed water is the same in all embodiments, the restricting aperture being the most critical part because of the smallest diameter.

As shown in FIG. 2, the restricting element 3 may also consist of a narrowed part 9 of the flow channel 1. This is a so-called Venturi tube, in which the losses are smaller because of the streamlined shape. Its sensitivity to moisture is, however, the same as in a detector with a restricting aperture as shown in FIG. 1.

FIG. 3 presents a flow measuring detector in which the restricting element 3 restricting flow in the flow channel consists of the measuring channel 4 orifices 10, which are placed in the flow. The orifices 10 are symmetrically arranged to permit flow measurement in both directions of the tube with the same sensitivity. The orifices 10, typically located in the centre of the flow channel tube 1, are connected to a measuring device 8 via measuring channel tubes 4. The orifices 10 are a variation of the Pitot tube. A detector like this has a relatively low flow resistance, but in the case of a rough flow profile, a measurement error will be produced. This is what occurs for instance in respiratory tract measurement, as is stated in specification U.S. Pat. No. 5,088,332. This solution is somewhat less sensitive to condensed water, but in principle its behaviour is similar to that of the detectors mentioned above.

The flow detector presented in FIG. 4 is based on laminar flow resistance. The restricting element 3 restricting flow has been constructed by dividing the interior space of the tube into a large number of small tubes 11, in each of which a laminar flow prevails in the relevant measurement range. However, as a consequence, the detector is liable to be blocked. It is clearly more sensitive to water drops than the other detector types described.

Based on the principle illustrated by FIG. 3, FIG. 5 and 6 present a flow measuring detector D with an improved construction, known from specification U.S. Pat. No. 5,088,332, which measures the mean value of the flow profile. FIG. 5 shows the detector in end view and FIG. 6 presents a longitudinal section of it, taken along line VI—VI. Placed near and around the orifices 12 acting as a restricting element 3 in the flow channel tube 1 are vanes 13 provided with a groove, this embodiment having three such vanes. This arrangement gathers the Pitot pressure evenly from all directions, and shifts in the flow profile have no effect on the result. It is also possible to connect to the detector a sampling tube 5 for the measurement of gas concentrations, and the detector is therefore connected to a spirometer and to the sampling adapter of a gas analyzer A.

FIG. 7 shows yet another embodiment of the measuring detector, which corresponds to the detector in FIG. 5 and 6 except that the measuring channel 5, constituting a sampler connected to a gas analyzer A, is disposed on a separate connection piece 20 connected between the intubation tube I and the measuring detector, corresponding to the system illustrated by FIG. 11, which will be described in greater detail later on.

Figure 9:
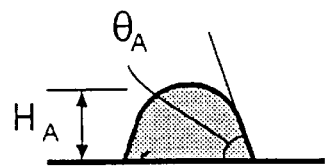
FIG. 9 illustrates the shape of a water drop on the surface a wall of a prior-art measuring detector.
Figure 10:
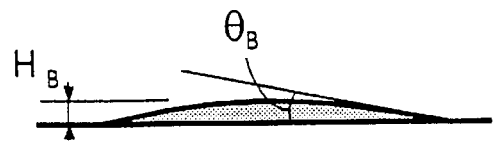
FIG. 10 illustrates the shape of a water drop on the surface of a wall of a measuring detector treated with an agent according to the invention.

The detector in FIG. 6 is sensitive to condensed moisture especially in measurements taking a long time. The detector material is preferably plastic, e.g. polysulfone. This material, like most other plastic materials, forms a nearly 90° contact angle θ with water. The situation is illustrated by FIG. 9, in which the contact angle is denoted as $\theta_A$. The contact angle of a water drop can be determined by the so-called sessile-drop method. The contact angle θ depends on the surface tensions between air, water and the detector material. The smaller the angle θ, the more is the water drop spread out along the surface of the detector material and the less will it affect the measurement accuracy. The drop height H directly reduces the diameter of the flow detector by the amount of about 2·H. It will therefore be readily understood that the height $H_B$ of the water drop presented in FIG. 10 has a much smaller effect because the contact angle $\theta_B$ is small. How small a contact angle value is to be reached depends on the measurement tolerance aimed at. In principle, the contact angle θ can even be reduced down to 0°. In this case, each water drop will spread unbounded, forming a film of water on the surface. Using a suitable agent, e.g. a surface-active agent, in the wall 2 of the measuring channel and/or in the restricting element 3, such a situation can be achieved. Water will still be condensed on the detector surface, but no drops can be formed and the extra water will readily flow out of the detector area.

Figure 8:
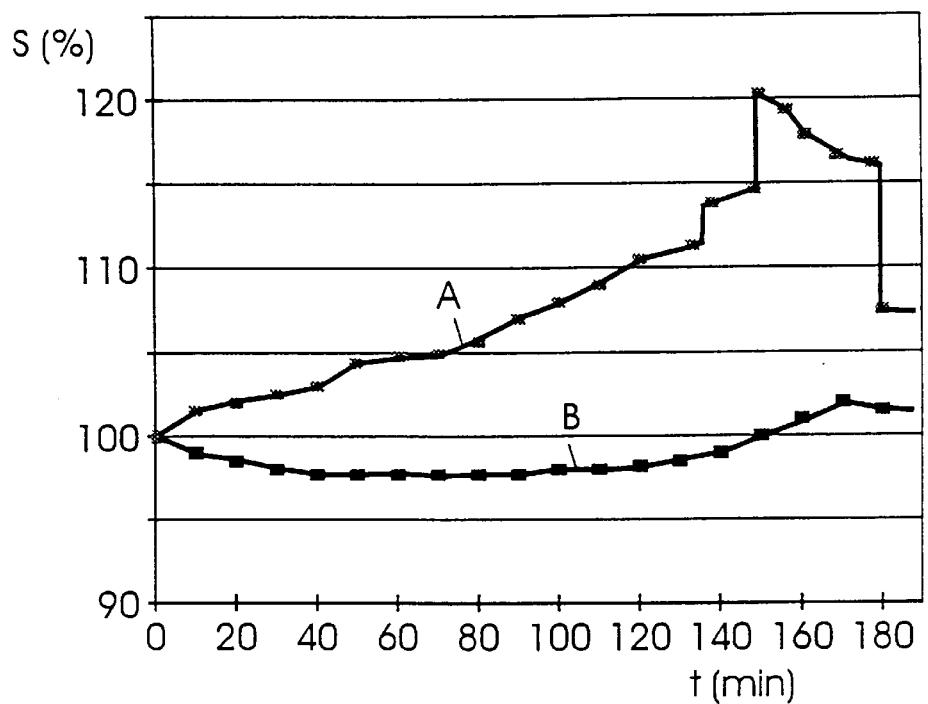
FIG. 8 presents signals measured with an uncoated measuring detector A and with a measuring detector B coated with a surface-active agent according to the invention, as functions of time.

FIG. 8 presents a couple of measuring periods as a function of time, representing measurements with a detector as shown in FIG. 6. The vertical axis in FIG. 8 gives a percentage representing the error level of the flow signal S, while the horizontal axis represents time in minutes. The gas used has been fully moistened at patient temperature, so condensation has occurred. Curve A has been measured using a measuring detector without a coating of surface-active agent. A more detailed description of the detector and the associated measuring arrangement is to be found in specification U.S. Pat. No. 5,088,332. FIG. 8 shows that the flow signal S has increased by 5% in the course of an hour. At 130 min and 140 min, small drops have combined and formed large ones, and at 175 min a few large drops have flowed out of the detector. The largest measured error is 20% and the signal varies all the time during about two hours from the beginning of the test. Curve B has been measured using a detector whose interior surface has been treated with a soap preparation reducing surface tension. In other words, the contact angle has as in FIG. 10, maybe even smaller, instead of FIG. 9. The falling trend of curve B at the beginning is not due to water drops but to changes in temperature. After about two hours, the curve starts rising due to the soap preparation being washed away. In any case, the test shows clearly that a coating that reduces the contact angle is of decisive importance in long-time use of the detector.

A coating reducing the contact angle θ of water should preferably be provided on the interior surface of the entire detector, but the most critical surfaces are those where the flow restricting element 3 is located and where the cross-sectional area is smallest. A coating or impregnation of the detector material with a surface-active agent can be applied to all the detectors presented in FIG. 1–7.

The contact angle θ between water and different sorts of plastic is generally large, i.e. >60°, sometimes >90°. Of course there are materials with a very small contact angle, but these materials are generally difficult to use. These include glass, which has a 0° contact angle, provided that the glass is absolutely clean. Even the slightest impurity, such as fat, immediately increases the contact angle. The coating is typically of a nature reducing surface tension. This group includes various soap preparations and chemical detergents. There are also preparations developed especially for antifogging, generally intended for optical use. One of these is Dr.Fog Endoscopic Antifog Solution, produced by O.R.Concepts Inc.. Although complete antifogging provides an advantage, it is not necessary if small contact angles θ are acceptable. For example, if the contact angle is <30°, the measurement accuracy can be considered as being clearly improved, so it will be useful to use a coating reducing the contact angle with materials having a contact angle larger than about 30°. When the contact angle achieved by the use of a coating is <20°, the detector surface will become quite easily watered and a fairly good measurement accuracy is achieved. However, the best result is achieved when the contact angle is 0° or close to it. Durability of the film may be a problem if the film is water soluble. In disposable detectors such a coating may be used, but for long-time use a coating immobilized on the surface is the right solution. This type of water insoluble films are available e.g. for protective spectacles. It is also possible to impregnate a plastic material with a chemical. In this case the coating will be more durable, even if part of it is solved in water and flows out from the detector, because more of the chemical exudes out of the material all the time. Such a detector could work e.g. for a few days, which in most cases is fully sufficient for a disposable detector.

Besides allowing water to flow out more readily from the coated detector, the more lubricious surface also allows easier removal of possible secretions. In the above description, only a few typical examples of measuring detectors using a flow restricting element are mentioned. It is obvious that even other types of detectors working on a corresponding principle will benefit from the use of a surface-active agent improving measurement accuracy according to the present invention.

Figure 11:
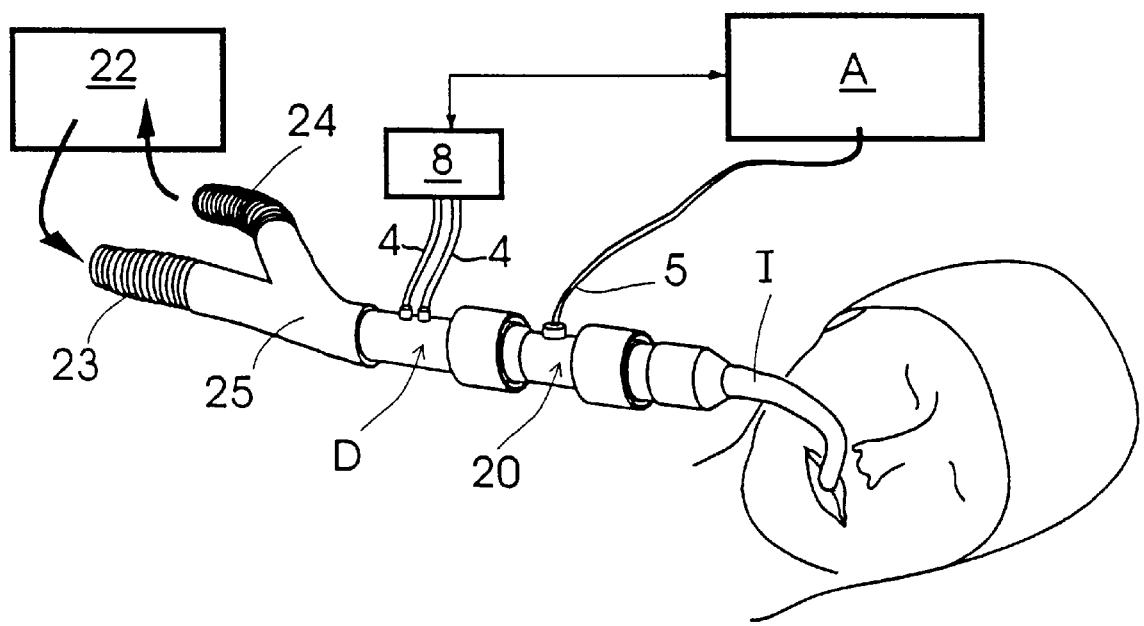
FIG. 11 is a diagram representing an embodiment of the system of the invention.

FIG. 11 presents a system according to the invention in a practical case, with an intubation tube I inserted into a patient's windpipe. Connected to the respiratory circuit is a measuring detector D corresponding to a spirometer detector treated on the inside with an agent, as shown e.g. in FIG. 7. A connecting piece 20, provided with a measuring channel 5 for the measurement of gas concentration, is connected between the intubation tube I and a Y-shaped piece 25 connecting the inlet and outlet hoses 23, 24 of an apparatus 22 maintaining respiration. The connecting piece 20 is normally so connected that it lies closest to the patient, but it could also be integrated with the flow detector D as in FIG. 6 or it could be placed between the flow detector and the Y-shaped piece 24. The gas sampler tube 5 is connected via a hose to a patient monitor or analyzer A, in which the gas is measured and the signal is processed so as to produce a display showing the variations in the gas concentration under measurement as a function of time, i.e. the respiration curve or concentration readings during inhalation and exhalation. The flow detector is also connected via the measuring apparatus 8 to the analyzer A, in which the signal is processed so as to produce a display of the flow and pressure readings for inhalation and exhalation and possible other quantities derived therefrom. The measuring device 8 may also be placed in the analyzer A and the gas concentration measurement can be performed in the connecting piece 20.

The invention is not restricted to the examples of its embodiments described above, but many variations are possible within the framework of the inventive idea defined by the claims.

I claim:

1. Measuring detector for the measurement of gas flow, especially for the measurement of the pressure and/or flow of a patient's respiratory gas, which measuring detector comprises a tubular flow channel (1) for guiding the gas flow to be measured, which flow channel is delimited by a wall (2); a restricting element (3) disposed in the flow channel to restrict gas flow in the flow channel; and measuring channels (4) opening into the flow channel for the measurement of the pressure difference caused by the restricting element, at least one of a surface of the flow channel wall (2) and/or the restricting element (3), said surface being in direct contact with the gas flow to be measured, being provided with an agent for reducing the contact angle ($\theta$) of a water drop or a drop containing water to said surface in relation to the contact angle formed between a corresponding water drop and a corresponding surface not treated with such agent.

2. Measuring detector as defined in claim 1, characterized in that the agent reduces the surface energy of a drop.

3. Measuring detector as defined in claim 1, characterized in that the agent increases the surface energy of said surface.

4. Measuring detector as defined in claim 2, characterized in that the agent is a surface-active agent that reduces the surface energy of a drop.

5. Measuring detector as defined in claim 1, characterized in that the agent is an antifogging agent immobilized on said surface.

6. Measuring detector as defined in claim 1, characterized in that the agent forms a film-like coating (P) on said surface.

7. Measuring detector as defined in claim 6, characterized in that the coating (P) formed by the agent is immobilized on the surface.

8. Measuring detector as defined in claim 1, characterized in that the material of the wall (2) and/or restricting element (3) is impregnated with the agent.

9. Measuring detector as defined in claim 1, characterized in that the agent is so selected that the contact angle of a water drop or a drop containing water to the surface in will be smaller than 30°.

10. Measuring detector as defined in claim 1, characterized in that the agent is a surface-active agent soluble in water.

11. Measuring detector as defined in claim 10, characterized in that the surface-active agent consists of molecules containing an oleo-philic hydrophobic group, such as an alkyl chain, and a hydrophilic group, such as a negatively charged carboxylic or sulphonic acid group.

12. Measuring detector as defined in claim 4, characterized in that the surface-active agent contains a detergent, such as soap or a similar wash agent.

13. Measuring detector as defined in claim 1, characterized in that the measuring detector (D) is a spirometer detector connected to an intubation tube (I) which can be inserted into a patient's windpipe.

14. Measuring detector as defined in claim 13, characterized in that it comprises a measuring channel (5) connected to the measuring detector (D) and functioning as a sampler for a gas analyzer (A).

15. Measuring detector as defined in claim 1, characterized in that the measuring detector (D) is a detector working on the Pitot tube principle, based on the measurement of Pitot pressure, in which the flow restricting element (3) consists of one or more vanes (13) directed against the flow.

16. Measuring detector as defined in claim 15, characterized in that the restricting element (3) is provided with vanes (13) arranged radially around the orifice (12) of the measuring channel (5), and that each vane (13) is provided with a groove (14) for directing the gas flow hitting the vanes into the orifice.

17. System for the measurement of the pressure and/or flow of a patient's respiratory gas, which system comprises an intubation tube (I) designed to be inserted into a patient's windpipe; a measuring detector (D) connected to the intubation tube and comprising: a tubular flow channel (1) for guiding the gas flow to be measured, said flow channel being delimited by a wall (2); a restricting element (3) disposed in the flow channel to restrict gas flow in the flow channel; a measuring device (8) for measuring the pressure difference caused by the restricting element; and measuring channels (4) opening into the flow channel for passing the pressure from the flow channel into the measuring device, at least one of a surface of the flow channel wall (2) and the restricting element (3), said surface being in direct contact with the gas flow to be measured, being provided with an agent for reducing the contact angle (θ) of a water drop or a drop containing water to said surface in relation to the contact angle formed between a corresponding water drop and a corresponding surface not treated with such agent.

18. System as defined in claim 17, characterized in that the agent reduces the surface energy of a drop.

19. System as defined in claim 17, characterized in that the agent increases the surface energy of said surface.

20. System as defined in claim 18, characterized in that the agent is a surface-active agent that reduces the surface energy of a drop.

21. System as defined in claim 17, characterized in that the agent is an antifogging agent immobilized on said surface.

22. System as defined in claim 17, characterized in that the agent forms a film-like coating (P) on said surface.

23. System as defined in claim 22, characterized in that the coating (P) formed by the agent is immobilized on the surface.

24. System as defined in claim 17, characterized in that the material of the wall (2) and/or restricting element (3) is impregnated with the agent.

25. System as defined in claim 17, characterized in that the agent is so selected that the contact angle (θ) of a water drop or a drop containing water to the surface will be smaller than 30°.

26. System as defined in claim 17, characterized in that the agent is a surface-active agent soluble in water.

27. System as defined in claim 17, characterized in that the measuring detector (D) is a spirometer detector connected to an intubation tube (I) inserted into a patient's windpipe.

28. System as defined in claim 27, characterized in that it comprises a measuring channel (5) connected to the measuring detector (D) and acting as a sampler for a gas analyzer (A).

29. System as defined in claim 17, characterized in that the measuring detector (D) is a detector working on the Pitot tube principle, based on the measurement of Pitot pressure, in which the flow restricting element (3) consists of one or more vanes (13) directed against the flow.

30. System as defined in claim 17, characterized in that the system includes a gas analyzer (A) for the determination of the composition of respiratory gas.

31. System as defined in claim 30, characterized in that the measuring channel (5) functioning as a sampler for the gas analyzer (A) is disposed between a respiration apparatus (22) and the patient.

32. System as defined in claim 30, characterized in that the measuring channel (5) functioning as a sampler for the gas analyzer (A) is disposed between the intubation tube (I) and a respiration apparatus (22).

33. Measuring detector as defined in claim 4, characterized in that the agent is an antifogging agent immobilized on said surface.

34. Measuring detector as defined in claim 2, characterized in that the agent is a surface-active agent soluble in water.

35. Measuring detector as defined in claim 9, characterized in that the agent is a surface-active agent soluble in water.

36. Measuring detector as defined in claim 6, characterized in that the surface-active agent contains a detergent, such as soap or a similar wash agent.

37. Measuring detector as defined in claim 9, characterized in that the surface-active agent contains a detergent, such as soap or a similar wash agent.

38. System as defined in claim 18, characterized in that the agent is an antifogging agent immobilized on said surface.

39. System as defined in claim 18, characterized in that the agent is a surface-active agent soluble in water.

40. Measuring detector as defined in claim 9 characterized in that the agent is so selected that the contact angle of a water drop or a drop containing water to the surface will be smaller than 20°.

41. A measuring detector as defined in claim 40 characterized in that the agent is so selected that the contact angle of a water drop or a drop containing water to the surface will be smaller than 10°.

42. A measuring detector as defined in claim 41 characterized in that the agent is so selected that the contact angle of a water drop or a drop containing water to the surface will be about 0°.

43. The system as defined in claim 25 characterized in that the agent is so selected that the contact angle of a water drop or a drop containing water to the surface will be smaller than 20°.

44. The system detector as defined in claim 43 characterized in that the agent is so selected that the contact angle of a water drop or a drop containing water to the surface will be smaller than 10°.

45. The system as defined in claim 44 characterized in that the agent is so selected that the contact angle of a water drop or a drop containing water to the surface will be about 0°.

* * * * *